US010487134B2

(12) United States Patent
Dietrich et al.

(10) Patent No.: US 10,487,134 B2
(45) Date of Patent: Nov. 26, 2019

(54) MODIFIED COLLAGEN

(71) Applicant: INNOCOLL PHARMACEUTICALS LIMITED, Athlone, County Roscommon (IE)

(72) Inventors: Alexandra Dietrich, Saal/Donau (DE); Michael Myers, Ashburn, VA (US)

(73) Assignee: INNOCOLL PHARMACEUTICALS LIMITED, Athlone, Co. Roscommon (IE)

( * ) Notice: Subject to any disclaimer, the term of this patent is extended or adjusted under 35 U.S.C. 154(b) by 648 days.

(21) Appl. No.: 14/371,161

(22) PCT Filed: Jan. 9, 2013

(86) PCT No.: PCT/EP2013/050333
§ 371 (c)(1),
(2) Date: Jul. 8, 2014

(87) PCT Pub. No.: WO2013/104687
PCT Pub. Date: Jul. 18, 2013

(65) Prior Publication Data
US 2015/0011476 A1    Jan. 8, 2015

(30) Foreign Application Priority Data

Jan. 9, 2012  (EP) .................................. 12150527
Nov. 20, 2012  (GB) .................................. 1220868.2

(51) Int. Cl.
| C07K 1/12 | (2006.01) |
| C07K 14/78 | (2006.01) |
| C08L 89/00 | (2006.01) |
| C08L 89/06 | (2006.01) |
| A61L 27/24 | (2006.01) |
| A61K 31/445 | (2006.01) |
| A61K 31/7036 | (2006.01) |
| A61K 47/42 | (2017.01) |
| A61L 27/54 | (2006.01) |
| A61K 38/39 | (2006.01) |

(52) U.S. Cl.
CPC .......... *C07K 14/78* (2013.01); *A61K 31/445* (2013.01); *A61K 31/7036* (2013.01); *A61K 47/42* (2013.01); *A61L 27/24* (2013.01); *A61L 27/54* (2013.01); *C08L 89/00* (2013.01); *C08L 89/06* (2013.01); *A61K 38/39* (2013.01); *A61L 2300/204* (2013.01); *A61L 2300/23* (2013.01); *A61L 2300/402* (2013.01); *A61L 2300/406* (2013.01)

(58) Field of Classification Search
None
See application file for complete search history.

(56) References Cited

U.S. PATENT DOCUMENTS

| 5,206,028 | A | 4/1993 | Li |
| 6,936,271 | B1 * | 8/2005 | Oliver et al. ................. 424/426 |
| 2001/0014667 | A1 * | 8/2001 | Chen ....................... A61L 27/24 600/431 |
| 2005/0208114 | A1 * | 9/2005 | Petito et al. ................... 424/445 |
| 2006/0008445 | A1 * | 1/2006 | Garralda ................. A01K 85/00 424/84 |
| 2010/0063253 | A1 |  3/2010 | Lin et al. |

FOREIGN PATENT DOCUMENTS

| EP | 0686402 A1 | 12/1995 |
| WO | WO 98/31403 A1 | 7/1998 |
| WO | WO 2011/014155 A1 | 2/2011 |
| WO | WO 2011014155 A1 * | 2/2011 |
| WO | WO 2011/139228 A1 | 11/2011 |

OTHER PUBLICATIONS

Cunningham, Leon W. and Ford, John D.; "A comparison of glycopeptides derived from soluble and insoluble collagens." J. Biol. Chem. (1968) 9(10) p. 2390-2398.*
The World Health Organization technical report "Stability testing of active pharmaceutical ingredients and finished pharmaceutical products." (2009) series No. 953, p. 87-130.*
Fegonezi-Nery, Marlene Maria et al, "Sensory evaluation of albendazole suspensions." Brazilian Archives of Biology and Technology (2002) 45(4) p. 457-463.*
The web page from Millrock technology on freezedrying, http://www.contractlyo.com/what-is-freeze-drying/, available online Jan. 14, 2011.*
The webpage "Introduction to lyophilization" http://www.sublimationscience.com/Teaching/Introduction%20to%20Lyophilization/Introduction.html, available online Mar. 2009.*
Zayas, Joseph F., Chapter 2, "Water holding capacity of proteins." in "Functionality of proteins in food." (1997) ISBN 978-642-63856-5.*
Miller-Chou, Beth A. and Loenig, Jack L.; "A review of polymer dissolution." Prog. Polym. Sci. (2003) 28 p. 1223-1270.*
Gebben, Bert et al, "Intramolecular crosslinking of poly(vinyl alcohol)." Polymer (1985) 26 p. 1737-1740.*

(Continued)

*Primary Examiner* — Fred H Reynolds
(74) *Attorney, Agent, or Firm* — Foley & Lardner LLP

(57) ABSTRACT

The present invention relates to a modified collagen obtainable by providing isolated collagen; freezing the isolated collagen; dehydrating the frozen collagen; and maturing the dehydrated collagen. Also disclosed are methods of preparing the modified collagen and uses thereof.

17 Claims, 12 Drawing Sheets

(56) References Cited

OTHER PUBLICATIONS

Wagner, Herman L., "The mark-houwink-sakurada equation for the viscosity fo linear polyethylene." J. Phys. Chem. Ref. Data (1985) 14(2) p. 611-617.*

Chvapil, M. et al, "Effect of collagen crosslinking on the rate of resorption of implanted collagen tubing in rabbits." J. Biomed. Mater. Res. (1977) 11 p. 297-314.*

Noishiki, Yashuharu et al, "Succinylated collagen crosslinked by thermal treatment for coating vascular prostheses." Artif. Organ (1998) 22(8) p. 672-680.*

The webpage describing the science module for middle school chemistry related to dissolution, http://middleschoolchemistry.com/lessonplans/chapter5/lesson6, available online Nov. 10.*

Einstein, A, "On the movement of small particles suspended in stationary liquids required by the molecular-kinetic theory of heat." Ann. Phys. (1905) 549-560.*

Theis, Edwin R. and Jacoby, T. F., "The acid-, base, and salt-binding capacity of salt-denatured collagen," Journal of Biological Chemistry (1943) 3 p. 603-700).*

Pekan, Onder and Ugur, Saziye, "Molecular weight effect on polymer dissolution: a steady state fluroescence study." Polymer (2002) 43 p. 1937-1941.*

Lim, Jong J. and Shamos, Morris H., "Evaluationof kinetic parameters of thermal decomposition of native collagen by thermogravimetric analysis." Biopolymers (1974) 13 p. 1791-1807.*

Quteish et al., "Development and Testing of a Human Collagen Graft Material," *J. Biomed. Mater. Res.* 24:749-760, 1990.

Schoof et al., "Control of Pore Structure and Size in Freeze-Dried Collagen Sponges," *J. Biomed. Mater. Res.* 58:352-357, 2001.

Uygur et al., "Use of Lyophilized Bovine Collagen for Split-Thickness Skin Graft Donor Site Management," *Burns* 34:1011-1014, 2008.

Arnold et al., "Evaluation of restorable barriers for preventing surgical adhesions," *Fertility and Sterility* 73(1):157-161 (Jan. 1, 2000).

European Search Report from European Patent Application No. 12150527.5, 12 pages (dated Jan. 17, 2013).

International Search Report from prior PCT Application No. PCT/EP2013/050333, 7 pages (dated Oct. 11, 2013).

Nalinanon et al., "Use of pepsin for collagen extraction from the skin of bigeye snapper (*Priacanthus tayenus*)," *Food Chemistry* 104(2):593-601 (May 3, 2007).

Osada et al., "Clinical evaluation of a haemostatic and anti-adhesion preparation used to prevent post-surgical adhesion," *Journal of International Medical Research* 27(5):247-252 (Sep. 1, 2009).

Written Opinion from prior PCT Application No. PCT/EP2013/050333, 7 pages (dated Oct. 11, 2013).

* cited by examiner

MODIFIED COLLAGEN

CROSS REFERENCE TO RELATED APPLICATIONS

This is the U.S. National Stage of International Application No. PCT/EP2013/050333, filed Jan. 9, 2013, which was published in English under PCT Article 21(2), which in turn claims the benefit of EP Application No. 12150527.5, filed Jan. 9, 2012 and GB Application No. 1220868.2, filed Nov. 20, 2012.

FIELD OF THE INVENTION

The present invention relates to a modified collagen obtainable by providing isolated collagen; freezing the isolated collagen; dehydrating the frozen collagen; and maturing the dehydrated collagen. Also disclosed are methods of manufacturing the modified collagen and uses thereof.

BACKGROUND TO THE INVENTION

Processes for the preparation of collagen-based materials for use in human and veterinary medicine by drying or lyophilizing aqueous collagen dispersions to create membranes or sponges are well known in the art. The use of collagen-based films or membranes as temporary, biodegradable barriers for separating apposing traumatized tissue surfaces following surgery to prevent or reduce the formation of postoperative adhesions is also known.

Typically, the collagen used for subsequent manufacture of the collagen-based materials is first isolated by extraction from mammalian hide or tendon, purified, enzymatically-treated to remove the non-helical telopeptides, partially solubilised with acid, and finally precipitated by increasing the pH to provide an aqueous dispersion of purified, fibrillar collagen. Once isolated, the collagen dispersion may be further processed for the manufacture of collagen-based materials immediately, or is otherwise stored while waiting further processing. For storage convenience at commercial scale, the collagen dispersion is normally concentrated by removal of water using centrifugation to reduce bulk and thereby create a wet mass. The wet mass must be stored frozen to preserve the collagen and prevent bacterial growth. When needed for manufacture of collagen-based materials, the frozen collagen wet mass is typically thawed and redispersed. Whether the isolated collagen is used immediately or frozen and thawed as a wet mass, the collagen dispersion is generally viscous and difficult to process at commercial scale into collagen-based membranes or lyophilized sponges. What is needed is a method to reduce the viscosity of the collagen dispersion without further dilution, since reducing the collagen concentration in the dispersion will only increase the amount of water that must be removed on subsequent drying or lyophilizing, which is both inefficient and costly at commercial scale.

Therefore, the object of the present invention is to modify the isolated collagen in such a way as to reduce the viscosity of the dispersion, but without compromising the properties of the collagen-based materials made thereof. Preferably, a further object of the present invention is to modify the collagen in such a way as to reduce the viscosity of the dispersion and also improve the properties of a collagen membrane made thereof for use as a postoperative adhesion barrier.

These objects are solved according to the present invention by providing a modified collagen that facilitates the efficient manufacture of collagen-based materials at commercial scale and improves the potential effectiveness of those materials in the field of human and veterinary medicine.

SUMMARY OF THE INVENTION

According to a first aspect of the present invention there is provided a modified collagen obtainable by providing isolated collagen, optionally an isolated collagen dispersion; freezing the isolated collagen; and dehydrating the frozen collagen.

According to a second aspect of the present invention there is provided a modified collagen obtainable by providing isolated collagen, optionally an isolated collagen dispersion; freezing the isolated collagen; dehydrating the frozen collagen; and maturing the dehydrated collagen.

By the term "dispersion" is meant a mixture in which collagen particles are dispersed in a fluid, optionally a liquid, further optionally an aqueous, medium. The collagen particles may comprise collagen molecules, or aggregates thereof; which are dispersed in a fluid, optionally a liquid, further optionally an aqueous, medium. Optionally, the collagen particles, which are dispersed in a fluid, optionally a liquid, further optionally an aqueous, medium; have a length (or maximum dimension) of at least one micrometer.

By "maturing" is meant processing the dehydrated collagen under conditions suitable to allow ageing of the dehydrated collagen without substantial degradation or contamination.

According to a third aspect of the present invention there is provided a method for preparing a modified collagen, the method comprising the steps of:
   (a) providing isolated collagen, optionally an isolated collagen dispersion;
   (b) freezing the isolated collagen; and
   (c) dehydrating the frozen collagen.

According to a fourth aspect of the present invention there is provided a method for preparing a modified collagen, the method comprising the steps of:
   (a) providing isolated collagen, optionally an isolated collagen dispersion;
   (b) freezing the isolated collagen;
   (c) dehydrating the frozen collagen; and
   (d) maturing the dehydrated collagen.

Optionally, the providing step comprises the step of removing the fluid, optionally the liquid, further optionally the aqueous, medium; prior to the providing step. Further optionally, the providing step comprises the step of removing at least some of the fluid, optionally the liquid, further optionally the aqueous, medium; prior to the providing step. Still further optionally, the providing step comprises the step of removing at least some of the fluid, optionally the liquid, further optionally the aqueous, medium; prior to the providing step; to provide an isolated collagen dispersion.

Optionally, the providing step comprises the step of removing the fluid, optionally the liquid, further optionally the aqueous, medium; prior to the providing step to provide a dispersion having a concentration of about 3-30%, optionally 3-4%, (w/w) collagen particles.

Optionally, the freezing step comprises freezing to a temperature of about −33° C. to about −42° C. Further optionally, the freezing step comprises freezing to a temperature of about −38° C. Still further optionally, the freezing step comprises freezing at a rate of about 0.3° C. to about 1.5° C. per minute, optionally a rate of about 0.5° C. per minute.

Optionally, the dehydrating step comprises removing the aqueous phase. Further optionally, the dehydrating step comprises removing the aqueous phase by reducing the pressure. Still further optionally, the dehydrating step comprises removing the aqueous phase by reducing the pressure to about 0.05 to about 0.5 mbar. Still further optionally, the dehydrating step comprises removing the aqueous phase by applying a vacuum.

Optionally or additionally, the dehydrating step comprises increasing the temperature of the frozen collagen. Further optionally or additionally, the dehydrating step comprises increasing the temperature of the frozen collagen under vacuum. Still further optionally or additionally, the dehydrating step comprises increasing the temperature of the collagen to about +30° C. Still further optionally or additionally, the dehydrating step comprises increasing the temperature of the collagen to about +30° C. under vacuum.

Optionally or additionally, the dehydrating step comprises increasing the temperature of the collagen to about +30° C. at a rate of about 0.3° C. to about 1.5° C. per minute, further optionally at a rate of about 0.5° C. per minute. Further optionally or additionally, the dehydrating step comprises increasing the temperature of the collagen to about +30° C. at a rate of about 0.3° C. to about 1.5° C. per minute, further optionally at a rate of about 0.5° C. per minute, under vacuum.

Optionally, the dehydrating step comprises at least one equilibrating step.

Optionally, the at least one equilibrating step comprises maintaining the temperature at a constant temperature, sufficient to allow the frozen collagen to reach a desired temperature. Further optionally, the at least one equilibrating step comprises maintaining the temperature at a constant temperature for a sufficient period of time to allow the frozen collagen to reach a desired temperature. Still further optionally, the at least one equilibrating step comprises maintaining the temperature at a constant temperature for at least 10 mins, optionally at least 20 mins, further optionally at least 30 mins, still further optionally at least 45 mins, still further optionally at least 60 mins; to allow the frozen collagen to reach a desired temperature.

Optionally, the at least one equilibrating step is conducted when the temperature is increased to at least −20° C. Optionally or additionally, the at least one equilibrating step is conducted when the temperature is increased to at least −10° C. Optionally or additionally, the at least one equilibrating step is conducted when the temperature is increased to at least 0° C. Optionally or additionally, the at least one equilibrating step is conducted when the temperature is increased to at least +10° C. Optionally or additionally, the at least one equilibrating step is conducted when the temperature is increased to at least +20° C. Optionally or additionally, the at least one equilibrating step is conducted when the temperature is increased to at least +30° C.

Optionally, the dehydrating step comprises six equilibrating steps, each equilibrating step being conducted when the temperature is increased by about 10° C. Further optionally, the dehydrating step comprises six equilibrating steps, each equilibrating step being conducted when the temperature is increased to about −20° C., about −10° C., about 0° C., about +10° C., about +20° C., and about +30° C.

Optionally, the maturing step comprises storing the dehydrated collagen at a temperature of at least 2° C. Further optionally, the maturing step comprises storing the dehydrated collagen at a temperature of at least 10° C. Still further optionally, the maturing step comprises storing the dehydrated collagen at a temperature of at least 20° C. Still further optionally, the maturing step comprises storing the dehydrated collagen at a temperature of at least 30° C. Still further optionally, the maturing step comprises storing the dehydrated collagen at a temperature of at least 40° C. Still further optionally, the maturing step comprises storing the dehydrated collagen at a temperature of at least 50° C. Still further optionally, the maturing step comprises storing the dehydrated collagen at a temperature of at least 60° C. Still further optionally, the maturing step comprises storing the dehydrated collagen at a temperature of at least 70° C. Still further optionally, the maturing step comprises storing the dehydrated collagen at a temperature of at least 80° C.

Optionally, the maturing step comprises storing the dehydrated collagen at a temperature of at least 30° C. Further optionally, the maturing step comprises storing the dehydrated collagen at a temperature of at least 40° C. Still further optionally, the maturing step comprises storing the dehydrated collagen at a temperature of at least 65° C.

Optionally, the maturing step comprises storing the dehydrated collagen at a temperature of 30° C. Further optionally, the maturing step comprises storing the dehydrated collagen at a temperature of 40° C. Still further optionally, the maturing step comprises storing the dehydrated collagen at a temperature of 65° C.

Optionally, the maturing step is conducted for a period of at least one week, optionally at least two weeks, further optionally at least three weeks, still further optionally at least four weeks, still further optionally at least five weeks, still further optionally at least six weeks.

Optionally, the maturing step is conducted for a period of at least two months, optionally at least four months, further optionally at least six months, still further optionally at least twelve months.

Optionally, the maturing step is conducted for a period of one week, optionally two weeks, further optionally three weeks, still further optionally four weeks.

Optionally, the maturing step comprises storing the dehydrated collagen at a temperature of at least 2° C. for a period of at least six months. Further optionally, the maturing step comprises storing the dehydrated collagen at a temperature of 2° C. for a period of six months.

Optionally, the maturing step comprises storing the dehydrated collagen at a temperature of at least 30° C. for a period of at least two months. Further optionally, the maturing step comprises storing the dehydrated collagen at a temperature of 30° C. for a period of two months.

Optionally, the maturing step comprises storing the dehydrated collagen at a temperature of at least 40° C. for a period of at least six weeks. Further optionally, the maturing step comprises storing the dehydrated collagen at a temperature of 40° C. for a period of six weeks.

Optionally, the maturing step comprises storing the dehydrated collagen at a temperature of at least 65° C. for a period of at least one week. Further optionally, the maturing step comprises storing the dehydrated collagen at a temperature of 65° C. for a period of one week.

Optionally, the maturing step is conducted at a relative humidity of less than 100%, optionally less than 90%, further optionally less than 80%, still further optionally less than 70%, still further optionally less than 60%, still further optionally less than 50%, still further optionally less than 40%, still further optionally less than 30%.

By "relative humidity" is meant a measure of the maximum amount of water in a mixture of gas and water vapour, optionally at a given gas temperature and atmospheric pressure, optionally at constant atmospheric pressure, optionally expressed as a percentage of the maximum amount of water vapour within the gas at the given gas temperature and atmospheric pressure. For the purposes of this specification, the term "relative humidity" is intended to mean a measure of the amount of water vapour in a mixture of environmental air and water vapour, in which the maturing step is conducted, at a constant atmospheric pressure, and expressed as a percentage. For the purposes of this specification, atmospheric pressure understood to be about 980 to about 1040 millibars.

It is understood that, in conducting the maturing step, the parameters of temperature, time, pressure, and relative humidity are not necessarily mutually exclusive, and the skilled person would recognise that as one parameter is varied, one or both of the other parameters may also be varied accordingly.

Optionally, the maturing step comprises storing the dehydrated collagen at a temperature of at least 40° C. for a period of at least six weeks, and at a relative humidity of less than 80%. Further optionally, the maturing step comprises storing the dehydrated collagen at a temperature of 40° C. for a period of 6 weeks, and at a relative humidity of 75%.

Optionally, the isolated collagen is fibrillar collagen. Further optionally, the isolated collagen is selected from Type I collagen, Type II collagen, Type III collagen, and a mixture thereof. Still further optionally, the isolated collagen is Type I collagen.

Optionally, the method further comprises the step of mechanically degrading the modified collagen prior to the maturing step. Optionally, the mechanical degrading step comprises milling. Further optionally, the mechanical degrading step is selected from milling, cutting, grinding, and a mixture thereof.

According to a fifth aspect of the present invention there is provided a method for isolating collagen, the method comprising the steps of:
  (a) providing a collagen source; and
  (b) increasing the pH of the collagen source to about 6.5 to about 7.5.

Optionally, the collagen source is a collagen dispersion.

Optionally, the providing step comprises the step of removing the fluid, optionally the liquid, further optionally the aqueous, medium; prior to the providing step. Further optionally, the providing step comprises the step of removing at least some of the fluid, optionally the liquid, further optionally the aqueous, medium; prior to the providing step. Still further optionally, the providing step comprises the step of removing at least some of the fluid, optionally the liquid, further optionally the aqueous, medium; prior to the providing step; to provide an isolated collagen dispersion.

Optionally, the pH of the collagen source, optionally the collagen dispersion, is increased to about 7.5.

Optionally, the collagen source is a fibrous tissue, optionally connective tissue. Further optionally, the collagen source is tendon, optionally animal tendon, further optionally equine or bovine tendon, preferably equine tendon.

Optionally, the method comprises the step of degrading the collagen source prior to the pH-increasing step. Further optionally, the degrading step comprises mechanically degrading the collagen source prior to the pH-increasing step. Optionally or additionally, the degrading step comprises chemically degrading the collagen source prior to the pH-increasing step.

Optionally, the mechanical degrading step comprises milling. Further optionally, the mechanical degrading step is selected from milling, cutting, grinding, granulating, and a mixture thereof. Optionally or additionally, the chemical degrading step comprises contacting the collagen source with an enzyme, optionally a proteolytic enzyme. Optionally, the proteolytic enzyme is selected from chymosin, cathepsin E, and pepsin; preferably pepsin.

Optionally, the chemical degrading step is conducted at a pH of about 2.5.

Optionally, the method further comprises the step of removing contamination from the collagen source. Optionally, the removing step comprises contacting the collagen source with a base, optionally a strong base, further optionally sodium hydroxide, still further optionally an aqueous solution of sodium hydroxide.

Optionally, the method comprises the step of filtering the degraded collagen source, optionally the degraded collagen dispersion, prior to the pH-increasing step.

Optionally, the method comprises the step of concentrating the collagen. Optionally, the concentrating step comprises isolating the collagen. Further optionally, the concentrating step comprises isolating the collagen by centrifugation.

Optionally, the concentrating step comprises the step of removing the fluid, optionally the liquid, further optionally the aqueous, medium; to provide a dispersion having a concentration of about 3-30%, optionally 3-4%, (w/w) collagen particles.

Optionally, the isolated collagen is frozen. Further optionally, the isolated collagen is frozen at less than −20° C. Optionally, the frozen isolated collagen is thawed prior to preparing the modified collagen.

According to a sixth aspect of the present invention, there is provided a composition comprising a modified collagen according to a first aspect of the present invention, or a modified collagen prepared according to a second aspect of the present invention, for use in treating or preventing surgical adhesions.

Optionally, use comprises the administration of the composition at a biological membrane, optionally a biological tissue. Further optionally, use comprises the administration of the composition at a biological membrane, optionally a biological tissue, within a body cavity. Still further optionally, use comprises the administration of the composition at a biological membrane, optionally a biological tissue, within a body cavity such as a peritoneal cavity, a pericardial cavity, a uterine cavity, or a synovial cavity.

Optionally, use comprises the topical administration of the composition at a biological membrane, optionally a biological tissue. Further optionally, use comprises the topical administration of the composition at a biological membrane, optionally a biological tissue, within a body cavity. Still further optionally, use comprises the topical administration of the composition at a biological membrane, optionally a biological tissue, within a body cavity such as a peritoneal cavity, a pericardial cavity, a uterine cavity, or a synovial cavity.

According to a seventh aspect of the present invention there is provided a method for the manufacture of a composition comprising a modified collagen according to a first aspect of the present invention or a modified collagen prepared according to a second aspect of the present invention, the method comprising the steps of:
  (a) providing a modified collagen;
  (b) preparing an aqueous dispersion of the modified collagen;
  (c) degrading the aqueous dispersion; and
  (d) dehydrating the aqueous dispersion.

Optionally, the preparing step comprises adding heated water, optionally heated purified water, to the modified collagen. Optionally, the water, optionally the purified water is heated to about 35 to about 42° C. prior to adding to the modified collagen.

Optionally, the preparing step is conducted at a pH of about 4.0.

Optionally, the degrading step comprises mechanically degrading the aqueous dispersion.

Optionally, the mechanical degrading step comprises shear mixing.

Optionally, the composition comprises modified collagen in an amount of about 0.4% to 1.5% (w/w).

Optionally, the composition has a pH of about 4.0.

Optionally, the dehydrating step comprises removing liquid from the aqueous dispersion such that the composition comprises liquid in an amount of less than 30%, optionally less than 20%, further optionally less than 15% (w/w) of the composition. Further optionally, the dehydrating step comprises removing liquid from the aqueous dispersion such that the composition comprises liquid in an amount of less than 13%, preferably less than 12%, (w/w) of the composition.

Optionally, the dehydrating step comprises removing liquid from the aqueous dispersion using a convective drying cabinet.

According to an eighth aspect of the present invention there is provided a drug delivery composition obtainable by providing isolated collagen, optionally an isolated collagen dispersion; freezing the isolated collagen; and dehydrating the frozen collagen.

According to a ninth aspect of the present invention there is provided a drug delivery composition obtainable by providing isolated collagen, optionally an isolated collagen dispersion; freezing the isolated collagen; dehydrating the frozen collagen; and maturing the dehydrated collagen.

According to a tenth aspect of the present invention, there is provided a method of preparing a drug delivery composition for sustained drug release, the method comprising the steps of:
(a) providing isolated collagen, optionally an isolated collagen dispersion;
(b) freezing the isolated collagen; and
(c) dehydrating the frozen collagen.

According to an eleventh aspect of the present invention, there is provided a method of preparing a drug delivery composition for sustained drug release, the method comprising the steps of:
(a) providing isolated collagen, optionally an isolated collagen dispersion;
(b) freezing the isolated collagen;
(c) dehydrating the frozen collagen; and
(d) maturing the dehydrated collagen.

Optionally, the method further comprises the step of providing a drug, optionally a drug solution, to which the matured collagen is added, or which is added to the matured collagen.

Optionally, the drug is selected from an aminoglycoside antibiotic, or a salt or prodrug thereof; and an anaesthetic, or a salt or prodrug thereof.

Further optionally, the drug is selected from gentamicin ((3R,4R,5R)-2-{[(1S,2S,3R,4S,6R)-4,6-diamino-3-{[(2R,3R,6S)-3-amino-6-[(1R)-1-(methylamino)ethyl]oxan-2-yl]oxy}-2-hydroxycyclohexyl]oxy}-5-methyl-4-(methylamino)oxane-3,5-diol), or a salt or prodrug thereof; and bupivacaine ((RS)-1-butyl-N-(2,6-dimethylphenyl)piperidine-2-carboxamide), or a salt or prodrug thereof.

Optionally, the drug is an aqueous drug solution. Further optionally, the drug is an aqueous drug solution comprising an acid, optionally acetic acid.

Optionally, the method further comprises the step of mixing, optionally homogenizing, the drug-, optionally drug solution-, containing drug delivery composition.

Optionally, the method further comprises the step of lyophilizing and/or dehydrating, the drug-, optionally drug solution-, containing drug delivery composition.

BRIEF DESCRIPTION OF THE DRAWINGS

Embodiments of the present invention will now be described with reference to the following non-limiting examples and the accompanying drawings wherein the error bars represent standard deviations, in which.

EXAMPLES

Example 1—Collagen Isolation

Figure 1:
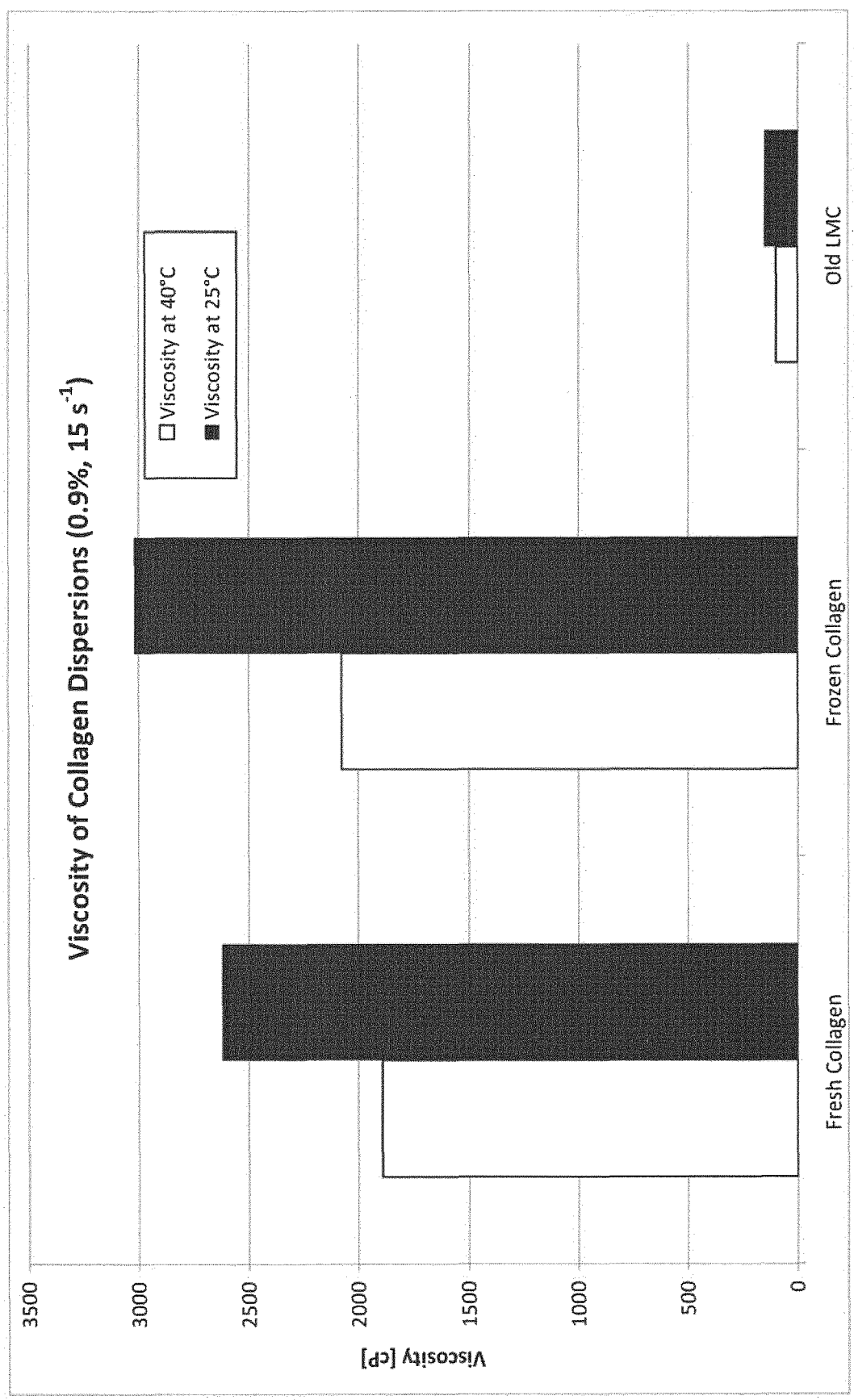
FIG. 1 is a graph illustrating the viscosity characteristic of compositions prepared from fresh collagen, frozen collagen, and dehydrated frozen collagen, which was allowed to age under ambient conditions for 3 years (old lyophilised milled collagen)

Collagen can be isolated from a number of sources, for example, animal hides and animal tendons. In a preferred embodiment, the collagen is isolated from animal tendon, for example equine or bovine tendon; although any known source of collagen, including fibrous tissue, optionally connective tissue, may be used and selected by one skilled in the art. Preferably, the collagen is isolated from equine tendon. In the method of isolation, equine tendons were milled to degrade the collagen source. The milled equine tendons were treated with a number of reagents, including 1N sodium hydroxide (NaOH) to remove microbiological contamination such as prions at the beginning of the process. Treatment steps with hydrogen peroxide and washing steps at different pH values were conducted, followed by a milling step, which was used to increase the surface for the next treatment step. The molecular weight of the collagen source was additionally reduced by treatment with the proteolytic enzyme pepsin at an approximate pH of 2.5. The pH was adjusted using an aqueous solution of 1N HCl. The pepsin was used to degrade contaminating serum components such as equine serum albumin (ESA) and resulted in the detachment of non-helical portions of the collagen molecule (telopeptides). During this process, the collagen material was also partially solubilised in the acidic medium. After filtration, the pH level was increased from 2.5 to 7.5 by addition of 1N sodium hydroxide (NaOH). This pH adjustment resulted in precipitation of the fibrillar collagen out of solution, which was then concentrated by means of centrifugation to provide a collagen dispersion having a concentration of about 3-30% (w/w). The resulting material was designated fresh collagen. The fresh collagen can be processed in several ways.

The fresh collagen can be packaged in suitable portions and frozen to −20° C. to be stored in a freezer until required for use. The resulting material was designated frozen collagen (FWC). The frozen collagen is thawed prior to use in the same manner as fresh collagen.

Alternatively, frozen collagen can be freeze-dried (lyophilised), and optionally subsequently milled. For this purpose, frozen collagen was manually distributed onto a flat surface, for example a polystyrene mould, the frozen collagen having a layer thickness of between about 5 mm and about 10 mm. The collagen-filled moulds were transferred onto the shelves of a commercially available freeze dryer (Christ Epsilon) and frozen to a temperature of about −38° C. with a ramp rate between 0.3° C. and 1.5° C. After an equilibration period of approximately 30 minutes vacuum was initiated and the shelf temperature was sequentially increased from about −38° C. to about +30° C. at a rate of about 0.5° C. per minute. The combination of vacuum and sequentially increasing the shelf temperature from about −38° C. to about +30° C. facilitated sublimation of the ice from the frozen collagen up until the collagen reached a temperature of 0° C. To ensure that the temperature of the collagen increased uniformly, at least one equilibrating step was conducted, in which the shelf temperature was maintained at a constant desired temperature for approximately 30 mins, or until the collagen reached the desired temperature. For example, an equilibrating step was conducted every 10° C. between the temperatures of −20° C. and +30° C. to ensure that the temperature of the collagen increased uniformly. The equilibrating step, for example at −20° C. comprised maintaining the shelf temperature at a constant temperature of −20° C. for about 30 mins. Once the ice had been removed by sublimation, and the collagen reached a temperature of 0° C., the residual water content was further reduced by continuing to sequentially increase the shelf temperature to about +30° C. at a rate of about 0.5° C. per minute. The lyophilised collagen was then milled using a commercially available cutting mill (Rotoplex, Hosokawa Alpine). The resulting material was designated non-matured lyophilised milled collagen (non-matured LMC).

Optionally, the non-matured lyophilised milled collagen was matured by storing in polyethylene containers (bags) under ambient conditions of about 2-8° C. at atmospheric pressure for periods of about 1-3 years until required for use. The resulting material was designated old lyophilized milled collagen (old LMC).

Alternatively, the non-matured lyophilized milled collagen (non-matured LMC) was matured by storing in polyethylene containers (bags) as described herein until required for use, for example stored at 40° C. for 2-6 weeks. The resulting material was designated matured lyophilized milled collagen (matured LMC).

Example 2—Compounding Process and Equipment

An aqueous modified collagen dispersion was prepared in a stainless steel vessel using pre-heated (35-42° C.) purified water, which was adjusted to pH 4.0±0.2. High shear mixing was required to break up the modified collagen mass and expose the collagen fibres to the acidic medium. The high shear mixer (homogeniser) comprised a rotor/stator head that is designed to create high shear forces by pulling the modified collagen through the rotating homogeniser head and forcing the modified collagen against the proximal stationary stator head. It is this design that provided the high shear forces required to separate the fibrous collagen mass at the beginning of the aqueous dispersion preparation. However, other comparable mixing equipment may also be used; and can be selected by one skilled in the art. For example, an IKA Ultra-Turrax mixer may be used at a high speed for about 2 to about 5 minutes.

If required, although not essential, the resulting aqueous dispersion can be filtered and degassed, for example by using 250 micron filters and a suitable means of degassing, for example ultrasonication.

The collagen concentration in the final aqueous dispersion can be in the range of 0.4% to 1.5% and the pH can be in the range of 4.0±0.2. The final aqueous dispersion can be subsequently transferred to a closed jacketed stainless steel vessel, optionally where the jacket temperature is maintained at 37° C. and the aqueous dispersion is slowly agitated using a low shear setting.

The dispersion was filled into, for example 10×10 cm, blister trays or lyophilisation moulds using, for example, a positive displacement pump. The pump can be a valve-less pump, optionally having ceramic pistons. Alternatively, a peristaltic pump could also be used. The fill weight was adjusted based on the collagen content of the aqueous dispersion to achieve the target collagen content per area, for example about 0.1 to about 10.0 mg/cm$^2$, optionally about 4 mg/cm$^2$. Upon completion of the filling process, the filled blisters or moulds were placed into a convective drying cabinet. A commercially available drying cabinet (LabAir; Bleymehl) at 31° C. was utilized for this drying process. The drying step can typically require between 1 and 3 days to remove the excess water, which results in the finished composition, for example membrane, being retained in the blisters or moulds.

Following completion of the drying process, the blisters or moulds were removed from the drying cabinet. The resulting composition, for example membrane, was cut to the desired size, for example using a pneumatic dye. The packaging process was a two-step process comprising introduction to an inner and outer pouch packaging (ethylene oxide; EO type; PMS MEDICAL LTD) followed by pneumatic heat sealing. One side of the outer pouch comprised a transparent polyester or low-density polyethylene (LDPE) foil laminate with a high-density polyethylene (HDPE) strip seal. The other side was an opaque polyester or LDPE laminate. Other outer pouch packaging material can be used, including aluminum oxide coated polyethylene materials or, if E-beam radiation is used for sterilization, an aluminum outer pouch can be used. The pneumatic heat sealer facilitated the formation of a continuous seal at the open end of the pouch. The top part of the pouch included two holes or strips lined with a high-density polyethylene (HDPE) strip seal. These openings/windows were specifically designed for the EO gas sterilisation process and were gas permeable only. The permeability of the window facilitated permeation of the EO gas during the terminal EO sterilization process. Following sterilization and ventilation, the outer pouch was resealed below the gas permeable openings/windows, and this gas permeable (top) portion was then removed from the pouch. This resulted in a fully sealed outer pouch containing a terminally sterilized finished composition, for example membrane.

Ethylene Oxide (EO; $C_2H_4O$) is a gas that, at appropriate operating temperatures, sterilises via the action as a powerful alkylating agent. Under the correct conditions, cellular constituents of organisms such as nucleic acid complexes, functional proteins, and enzymes will react with ethylene oxide, causing the addition of alkyl groups. As a result of the alkylation, cell reproduction is prevented and cell death ensues. The sterilizer used in the present Examples was a DMB 15009 VD (DMB Apparatebau GmbH, Germany). A mixture of EO/CO$_2$ at a ratio of 15:85 was used as the sterilization gas over a period of 6 hours at 4 bar pressure. For successful completion of this process, the product needs to contain a moisture level of not less than 9%, which can be achieved by holding it in an area under controlled environmental conditions. Following the EO sterilization process, the product was ventilated for a minimum of 3 to 4 weeks to reduce the level of remaining ethylene oxide gas and any residues from the composition, for example membrane, and packaging materials.

Example 3—Characterisation

All compositions (membranes) were prepared from a 0.6% dispersion using the method described herein above. All tests on the collagen dispersion were conducted within 1 day after compounding; and all characterisation experiments with the membranes were performed within 1 month after membrane manufacture using unsterilised membranes.

Dispersion Viscosity

The viscosity values of 0.9% collagen dispersions prepared from each of the fresh collagen, frozen collagen, non-matured lyophilised milled collagen, and matured lyophilised milled collagen according to Example 2 were measured using a Brookfield viscometer (Digital Rheometer DV-III+ with associated TC-501 Circulating Bath). The viscosity values were measured at a constant shear rate (15 s$^{-1}$) and over a temperature range from 25 to 40° C. at 5° C. increments. 60 measurements per temperature were averaged to obtain reliable results.

Figure 4:
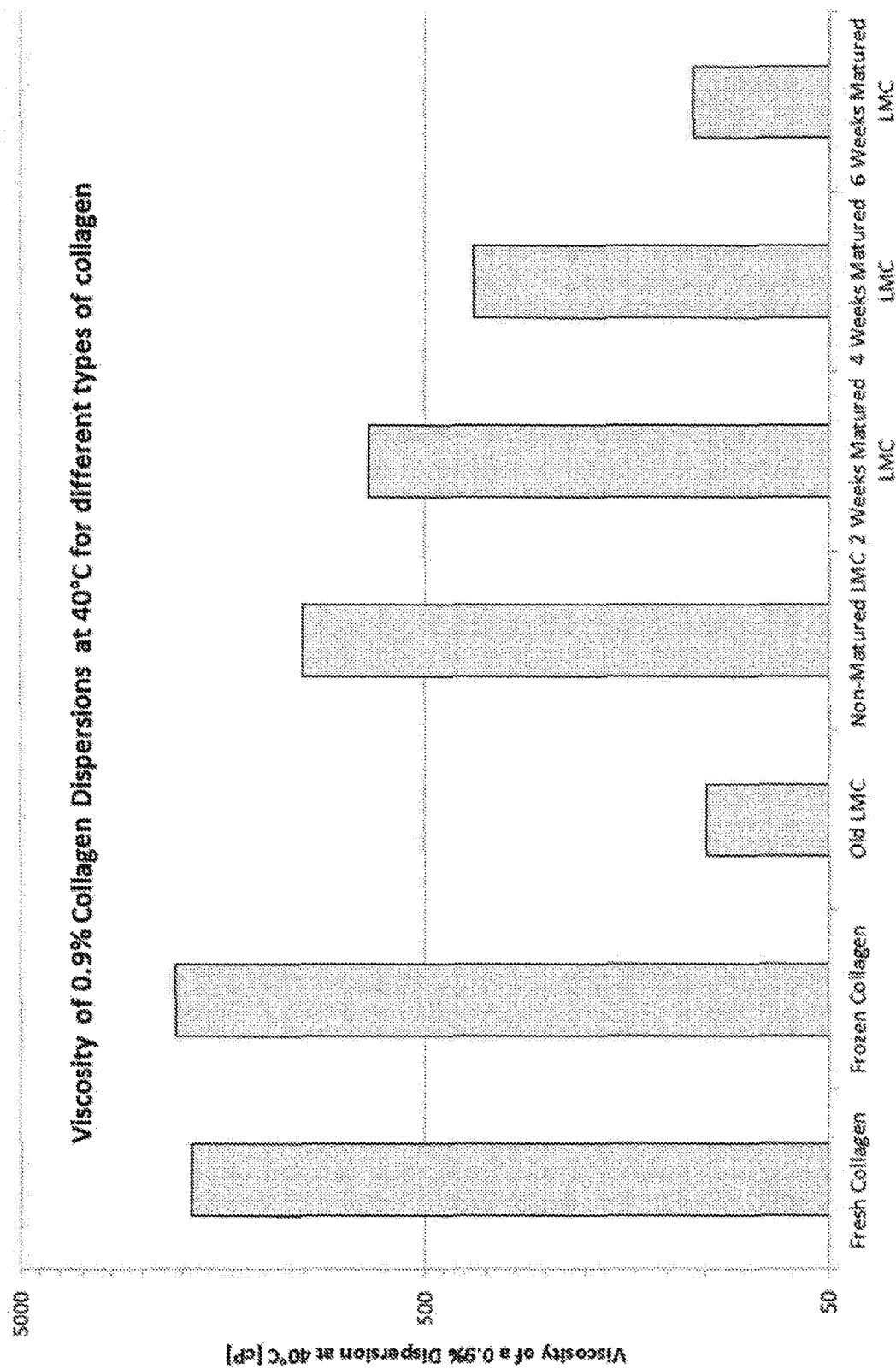
FIG. 4 is a graph illustrating the viscosity characteristic of compositions prepared from fresh collagen, frozen collagen, dehydrated frozen collagen, which was allowed to age under ambient conditions for 3 years (old lyophilised milled collagen), dehydrated frozen collagen (non-matured LMC), and a modified collagen according to a first aspect of the present invention, matured for 2, 4, and 6 weeks (LMC matured)

The dispersion viscosity depends on the temperature and decreases when heating up the dispersion. The viscosity profiles of fresh and frozen collagen are comparable over the temperature range tested. The lyophilised milled collagen, which was stored at a temperature of 2-8° C. for 3 years before compounding (old LMC), showed significantly lower viscosity at all investigated temperatures compared to the fresh collagen and the frozen collagen (see FIG. 1). Lyophilised milled collagen, which was compounded without storage (non-matured LMC), showed lower viscosity at all investigated temperatures compared to the fresh collagen and the frozen collagen (see FIG. 4). Lyophilised milled collagen, which was matured (stored at a temperature of 40° C. before compounding; matured LMC), showed lower viscosity compared to non-matured LMC (see FIG. 4), and comparable with old lyophilised milled collagen.

Figure 5:
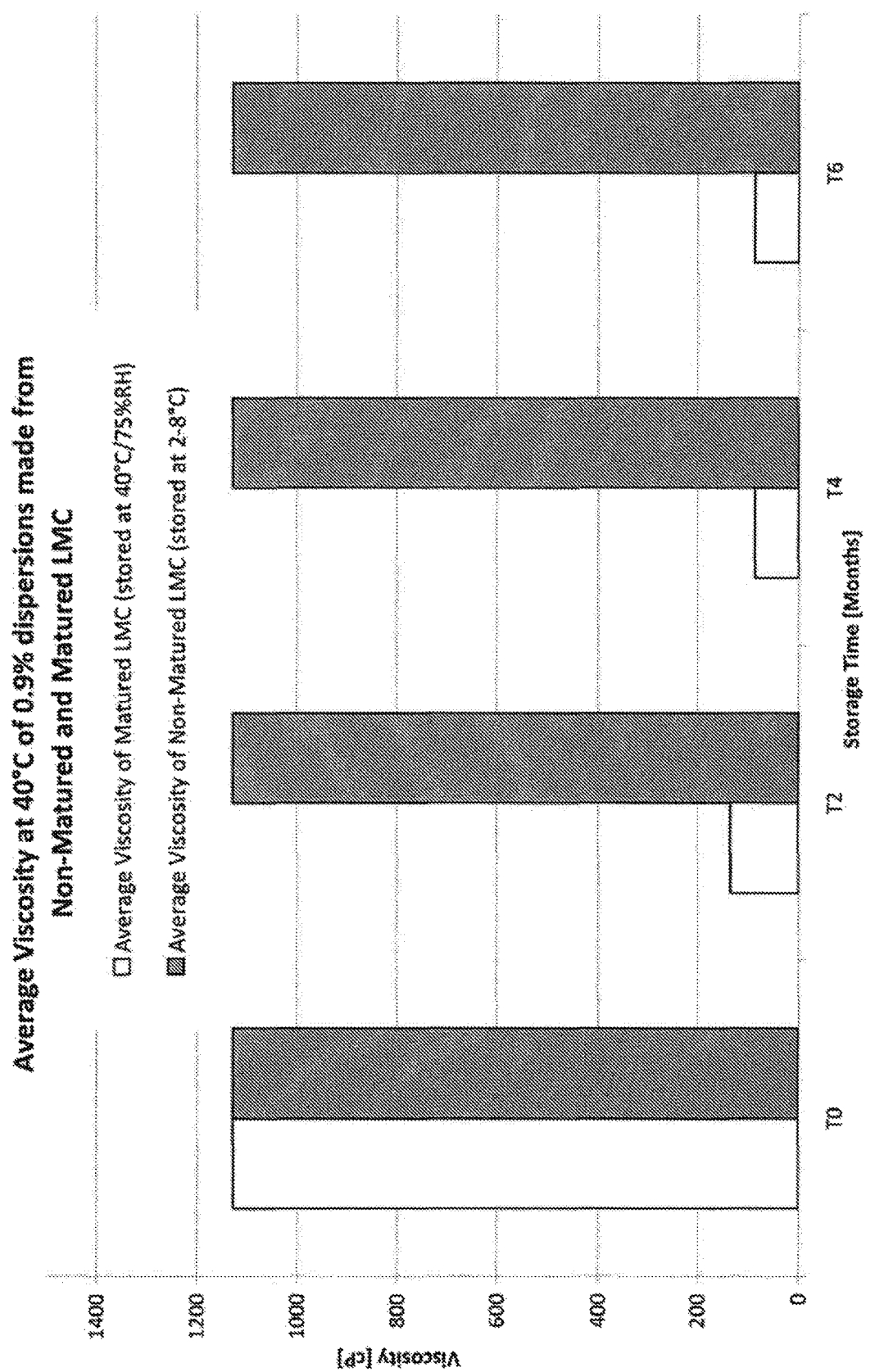
FIG. 5 is a graph illustrating the viscosity characteristic of compositions prepared from dehydrated frozen collagen (non-matured lyophilised milled collagen), and a modified collagen according to a first aspect of the present invention (LMC matured)

As can be seen in FIG. 5, maturing the lyophilised milled collagen as described herein results in improved viscosity at all investigated temperatures compared to non-matured lyophilised milled collagen, which is not subjected to the maturing step described herein.

The difference in viscosity is an advantage for processing of the membranes. Collagen with lower viscosity can be more easily degassed, and filled or casted; and the drying time is also reduced as collagens having higher concentrations can be processed. The modified collagen of the present invention provides improved viscosity characteristics compared to fresh collagen and frozen collagen; and the maturing step provides comparable viscosity characteristics compared to lyophilised milled collagen, which was stored at a temperature of 2-8° C. for 3 years before compounding (old LMC), thereby providing the improved viscosity characteristics of aged collagen (old LMC) without the extended ageing period.

Water Uptake and Swelling

Three rectangular samples (1.5×4 cm in size) were cut from 5 membranes prepared from each of the fresh collagen, frozen collagen, old lyophilised milled collagen, and matured lyophilised milled collagen. Each of these samples was soaked in WFI (water for injection) for 10 minutes, and analysed regarding water uptake (wet weight—dry weight) and swelling (wet thickness—dry thickness). The sample thickness was measured using a Mitutoyo Micrometer IP54.

Figure 2A:
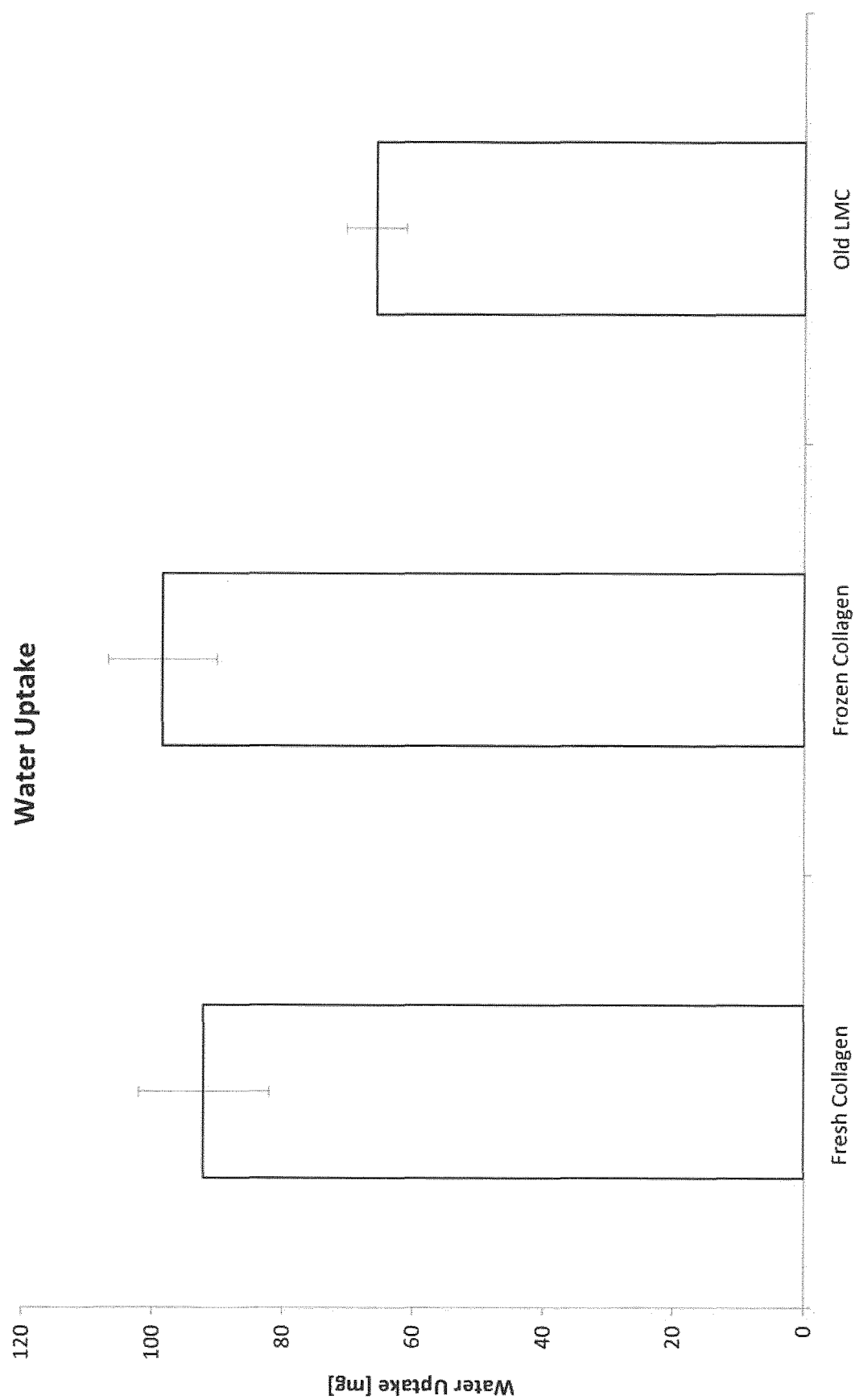
FIG. 2A is a graph illustrating the water uptake characteristic of compositions prepared from fresh collagen, frozen collagen, and dehydrated frozen collagen, which was allowed to age under ambient conditions for 3 years (old lyophilised milled collagen)
Figure 2B:
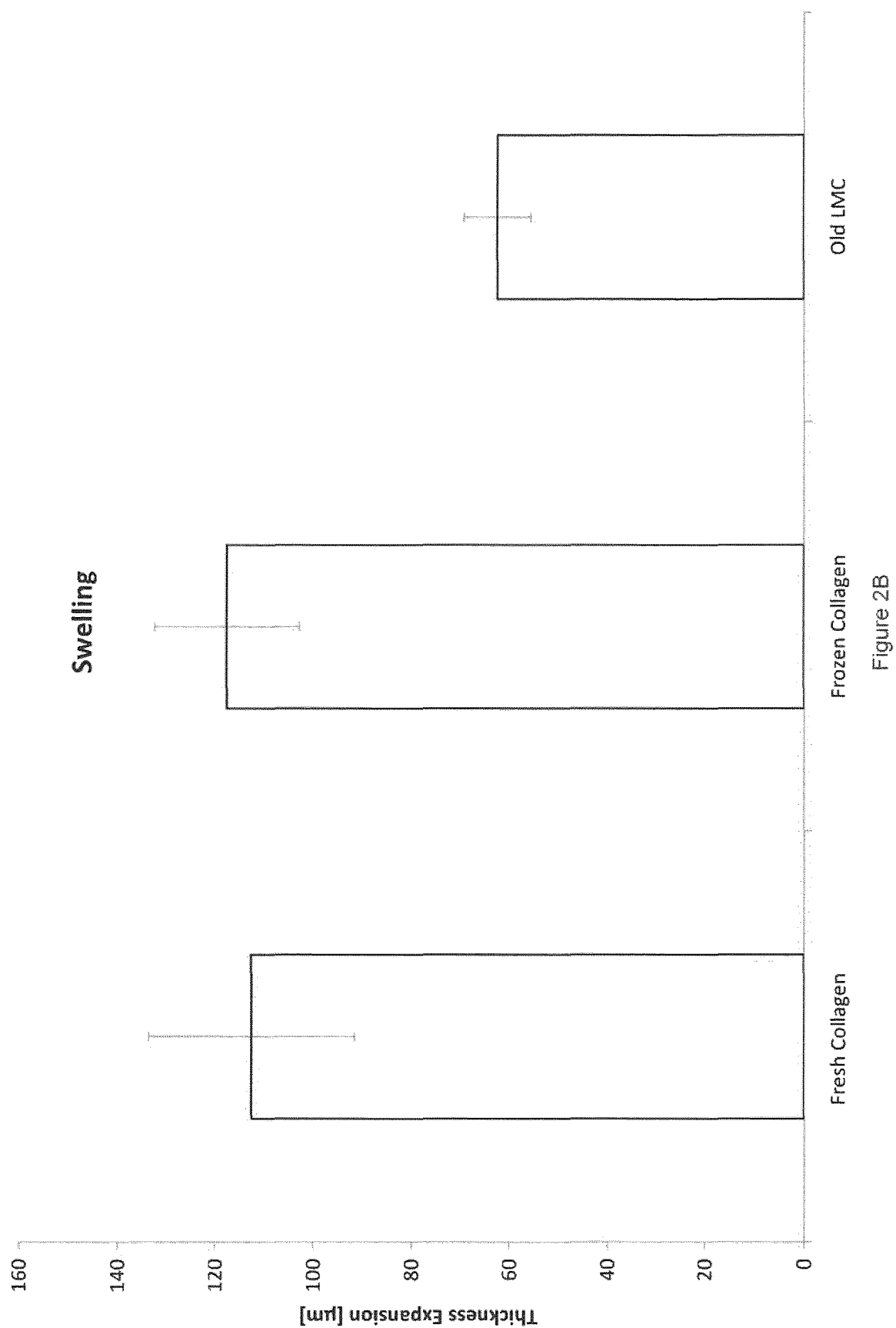
FIG. 2B is a graph illustrating the swelling characteristic of compositions comprising fresh collagen, frozen collagen, and dehydrated frozen collagen, which was allowed to age under ambient conditions for 3 years (old lyophilised milled collagen)

Membranes prepared from lyophilised milled collagen, which was stored at a temperature of 2-8° C. for 3 years before compounding (old LMC), showed lower water uptake and swelling than membranes prepared from fresh collagen and from frozen collagen (see FIGS. 2a and 2b). The variability of results was substantially lower for membranes prepared from lyophilised milled collagen, which was stored at a temperature of 2-8° C. for 3 years before compounding (old LMC) than for the membranes prepared from fresh collagen and from frozen collagen.

Figure 6:
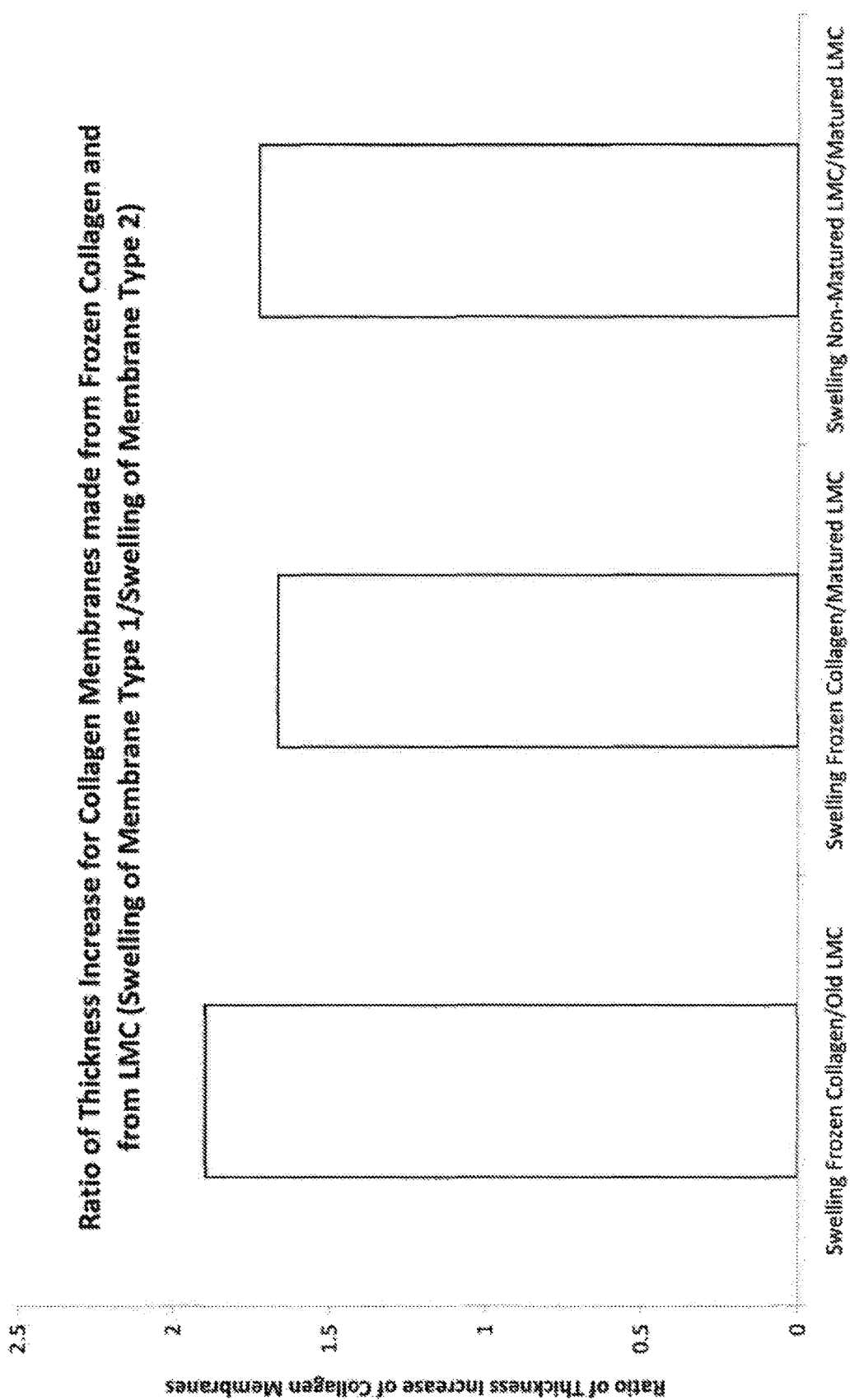
FIG. 6 is a graph illustrating the relative swelling ability of compositions prepared from frozen collagen (FWC) and dehydrated frozen collagen, which was allowed to age under ambient conditions for 3 years (old LMC); frozen collagen (FWC) and a modified collagen according to a first aspect of the present invention (LMC matured); and dehydrated frozen collagen (non-matured LMC) and a modified collagen according to a first aspect of the present invention (LMC matured)

As can be seen in FIG. 6, the thickness change for each collagen membrane tested demonstrates that the improved water uptake and swelling characteristics of membranes prepared from matured lyophilised milled collagen over membranes prepared from lyophilised milled collagen, which was stored at a temperature of 2-8° C. for 3 years before compounding (old LMC), are comparable to the improved water uptake and swelling characteristics of membranes prepared from matured lyophilised milled collagen over membranes prepared from frozen collagen.

The reduced swelling characteristics of membranes prepared from matured lyophilised milled collagen is advantageous as the membranes may be implanted into restricted anatomical spaces with a lower risk of pressurising and potentially damaging vital organs. Thus, for use in treating or preventing surgical adhesions, membranes prepared from the modified collagen may be used in a greater variety of anatomical geometries and surgical procedures.

Degradation with Collagenase

Degradation studies were conducted using 4 to 5 membranes per batch of each of the fresh collagen, frozen collagen, old lyophilised milled collagen, and matured lyophilised milled collagen. One membrane (4.5×4.5 cm in size) was placed into a beaker and covered with 15 mL of 0.2N Phosphate buffer (pH 7.4 with $CaCl_2$). Collagenase (Collagenase Type IA-S, sterile, 50 mg, SIGMA, REF C5894) was reconstituted with 5 mL of WFI, and 0.5 mL of the resulting solution was added to the mixture. The solution in the beaker was agitated using a shaking water bath (Julabo SW 22) at 37° C. (120 rpm) for 60 minutes. The degradation was documented by taking photographs of the samples every 5 minutes. Results are shown in Table 1. Membranes prepared from lyophilised milled collagen degraded the fastest with no residue, while membranes prepared from fresh collagen and frozen collagen degraded considerably slower, and left behind small fibre agglomerates.

TABLE 1

Degradation of equine collagen membranes in presence of Collagenase

| | Fresh Collagen | Frozen Wet Collagen | Old Lyophilized Milled Collagen |
|---|---|---|---|
| Dissolution [min] | 50 | 50 | 25 |

Figure 7:
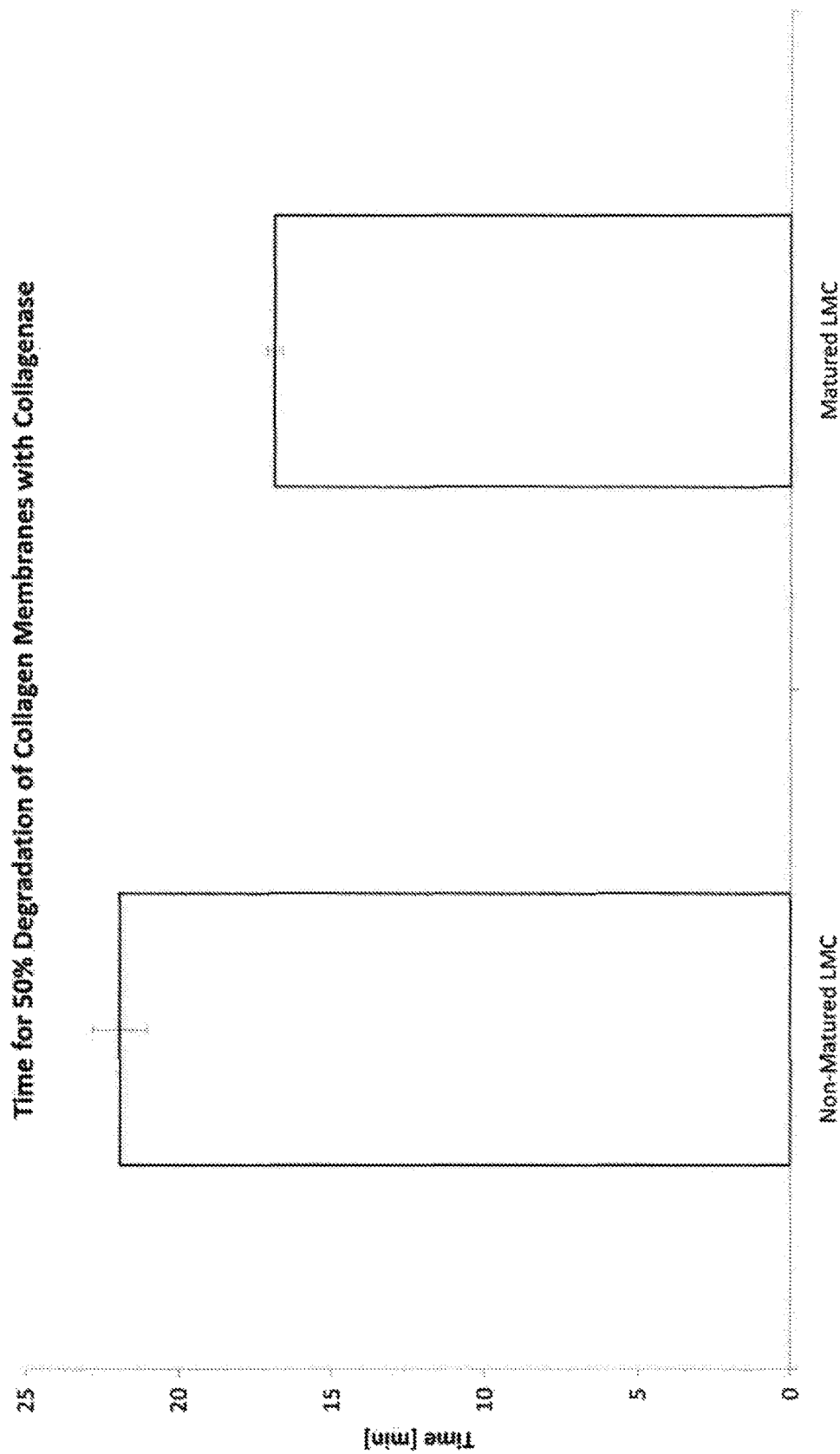
FIG. 7 is a graph illustrating the degradation characteristic of compositions prepared from dehydrated frozen collagen (non-matured LMC), and a modified collagen according to a first aspect of the present invention (LMC matured)

In a further study, 3.1×3.1 cm membrane samples were immersed in 15 mL of the buffer described above; to which 100 µL of reconstituted collagenase solution was added. 1 mL samples were removed after 5, 10, 15, 25, 40, 60, and 90 minutes; samples were filtered through a 0.45 µm syringe filter, and a 100 µL aliquot was diluted 1:30. UV absorption spectra between 210 and 230 nm (2 nm increments) were measured against a blank solution using a UV-VIS Photometer Specord 205 (Analytic Jena). The degraded fraction at each time point was calculated from the maximum absorption relative to the 90 minute time point (defined as 100%). The results can be seen in FIG. 7, which illustrated that membranes prepared from matured lyophilised milled collagen degraded faster than membranes prepared from lyophilised milled collagen.

A composition for use in treating or preventing surgical adhesions, for example a membrane for use as an adhesion barrier, needs to stay intact for a certain time in order to effectively inhibit adhesion. Prolonged presence of the membrane could lead to increased risk of infections, given that collagen is known to be a medium for bacterial growth. These in vitro experiments demonstrate that the membranes prepared from matured lyophilised milled collagen degrade faster than membranes prepared from old lyophilised milled collagen, and yet faster than membranes prepared from fresh collagen and frozen collagen, suggesting that this effect will also be true for the in vivo behaviour. Accordingly, a composition comprising a modified collagen according to a first aspect of the present invention, or a modified collagen prepared according to a second aspect of the present invention, for use in treating surgical adhesions, can reduce the probability of infections as an adverse effect of the use of the adhesion barrier.

Taken together, the examples provided herein demonstrate that a composition comprising a modified collagen according to a first aspect of the present invention, or a modified collagen prepared according to a second aspect of the present invention—for example, membranes prepared from matured lyophilised milled collagen—exhibit significantly altered properties compared to membranes made from fresh collagen, frozen collagen, or non-matured lyophilised milled collagen. The maturing step providing the altered properties of aged collagen without the extended ageing period; and so can be particularly useful in the manufacture of compositions for use in preventing or treating surgical adhesions.

Example 4—Dissolution

Preparation of Compositions Comprising Gentamicin

Compositions (sponges) containing gentamicin sulfate (Fujian Fukang Pharmaceutical Co. Ltd, China) were prepared for dissolution testing from a 1.6% w/w collagen dispersion using a modified version of the method described herein above. Each sponge measured 2.5×2.5×0.5 cm and contained 50 mg of collagen and 50 mg of gentamicin sulfate. In short, gentamicin sulfate (1.6% w/w) and 1N Acetic Acid were added to water for injection (WFI), and stirred until a clear solution resulted. Collagen (1.6% w/w) was added to the solution, either as frozen collagen (thawed directly prior to production); as non-matured Lyophilized Milled Collagen (non-matured LMC; lyophilized directly prior to production); or as a modified collagen according to the present invention (matured LMC). The mixture was homogenized using a commercially available high shear mixer (Ultraturrax, IKA, Germany) for 1 to 5 minutes at a temperature between 38 and 42° C. until a homogeneous viscous dispersion was obtained. The dispersion was filtered through a 250 µm mesh and stirred for approximately 30 minutes. Aliquots of the dispersion were filled into blisters and placed onto the shelves of a suitable freeze dryer and lyophilized. The blisters filled with dispersion were transferred onto the shelves of a commercially available freeze dryer and frozen to a temperature of about −38° C. with a ramp rate between 0.3° C. and 1.5° C. After an equilibration period of approximately 30 to 60 minutes, vacuum was initiated and the shelf temperature was sequentially increased from about −38° C. to about +30° C. at a rate of about 0.5° C. per minute. The combination of vacuum and sequentially increasing the shelf temperature from about −38° C. to about +30° C. facilitated sublimation of the ice from the frozen dispersion up until the product reached a temperature of 0° C. To ensure that the temperature of the collagen increased uniformly, at least one equilibrating step was conducted, in which the shelf temperature was maintained at a constant desired temperature for at least 30 mins, or until the collagen reached the desired temperature. The sponge-like porous composition was removed from the blister cavities and packed in pouches as described in Example 2 herein above.

Preparation of Compositions Comprising Bupivacaine

Compositions (sponges) containing bupivacaine HCl were produced for dissolution testing according to a similar method as described above. Sponges were produced from frozen collagen (FWC) and dehydrated frozen collagen, which was allowed to age under ambient conditions for 3 years (old LMC). Each sponge measured 5×5×0.5 cm and contained 75 mg of collagen and 100 mg of bupivacaine HCl (see FIG. 3). Sponges were also produced from dehydrated frozen collagen, which was allowed to age under ambient conditions for 3 years (old LMC) and dehydrated frozen collagen (non-matured LMC), measuring 10×10×0.5 cm and containing 100 mg bupivacaine-HCl and 300 mg collagen. (see FIG. 8B). In short, 1N Acetic Acid was added to WFI and briefly mixed. Collagen (0.6% w/w; either frozen collagen; Lyophilized Milled Collagen; or matured LMC) was added to the solution. The mixture was homogenized using a commercially available high shear mixer (Ultraturrax, IKA, Germany) for 1 to 5 minutes at a temperature between 38 and 42° C. until a homogeneous viscous dispersion was obtained. The dispersion was filtered through a 250 μm mesh.

Bupivacaine HCl (0.8% w/w) was dissolved in a small amount of WFI and added to the collagen dispersion. The mixture was stirred for approximately 30 minutes. Aliquots of the dispersion were filled into moulds and transferred onto the shelves of a commercially available freeze dryer and frozen to a temperature of about −38° C. with a ramp rate between 0.3° C. and 1.5° C. After an equilibration period of approximately 30 to 60 minutes vacuum was initiated and the shelf temperature was sequentially increased from about −38° C. to about +30° C. at a rate of about 0.5° C. per minute. The combination of vacuum and sequentially increasing the shelf temperature from about −38° C. to about +30° C. facilitated sublimation of the ice from the frozen dispersion up until the product reached a temperature of 0° C. To ensure that the temperature of the collagen increased uniformly, at least one equilibrating step was conducted, in which the shelf temperature was maintained at a constant desired temperature for at least 30 mins, or until the collagen reached the desired temperature. The sponge-like porous compositions were removed from the moulds and packed in pouches, as described in Example 2 herein above.

Gentamicin Dissolution Studies

The dissolution properties of compositions (sponges) containing gentamicin sulfate were analyzed in duplicate using a Dissolution Apparatus Type II (Distek Inc., USA), according to the manufacturer's instructions. To prevent the sponges from floating, they were placed into custom-made stainless steel sinkers. The weighted sponges were immersed in 500 mL of PBS Buffer (phosphate buffered saline, pH 7.4, bath temperature 37° C.) and stirred at 50 rpm for 24 hours. 4.0 mL sample was removed after 5, 10, 30, 45, 60, 120, 180, 240 and 1440 minutes. The samples were subjected to a chemical derivatisation reaction with Phthalaldehyde (4 mL sample+1.6 mL of a solution comprising 1% Phthalaldehyde+4.4 mL methanol) at 60° C. for 15 min (dilution 4/10). The resulting solutions were filtered and analyzed in a HPLC system (Shimadzu Corp., Japan), according to the manufacturer's instructions. A RP-18 HPLC column and a mobile phase comprising WFI, methanol, acetic acid and Na-1-heptanesulfonate with a flow rate of 0.5 mL/min was used. The gentamicin peaks C1, C2 and C2a at 330 nm were integrated, and the gentamicin concentration was calculated from the area under the curve of the samples and from a reference standard that was subjected to identical sample preparation.

Bupivacaine Dissolution Studies

The dissolution properties of compositions (sponges) containing bupivacaine HCl were analyzed in duplicate using a Dissolution apparatus Type II (Distek Inc., USA), as described above. To prevent the sponges from floating, they were placed into custom-made stainless steel sinkers. In short, the weighted sponges were immersed in 500 mL of PBS Buffer (phosphate buffered saline, pH 6.8, bath temperature 37° C.) and stirred with 50 rpm for 24 hours. 4.0 mL sample was removed after 5, 10, 30, 45, 60, 120, 180, 240 and 1440 minutes. The samples were diluted 1:1 with PBS buffer, filtered and analyzed in a HPLC system (Shimadzu Corp., Japan). A RP-18 HPLC column and a mobile phase comprising phosphate buffer pH 4.5 and acetonitrile with a flow rate of 0.5 mL/min was used. The bupivacaine peak at 230 nm was integrated, and the bupivacaine concentration was calculated from the area under the curve of the samples and from a reference standard.

The results of the dissolution studies are illustrated in FIGS. 3A, 3B, and 8A and 8B.

Figure 3A:
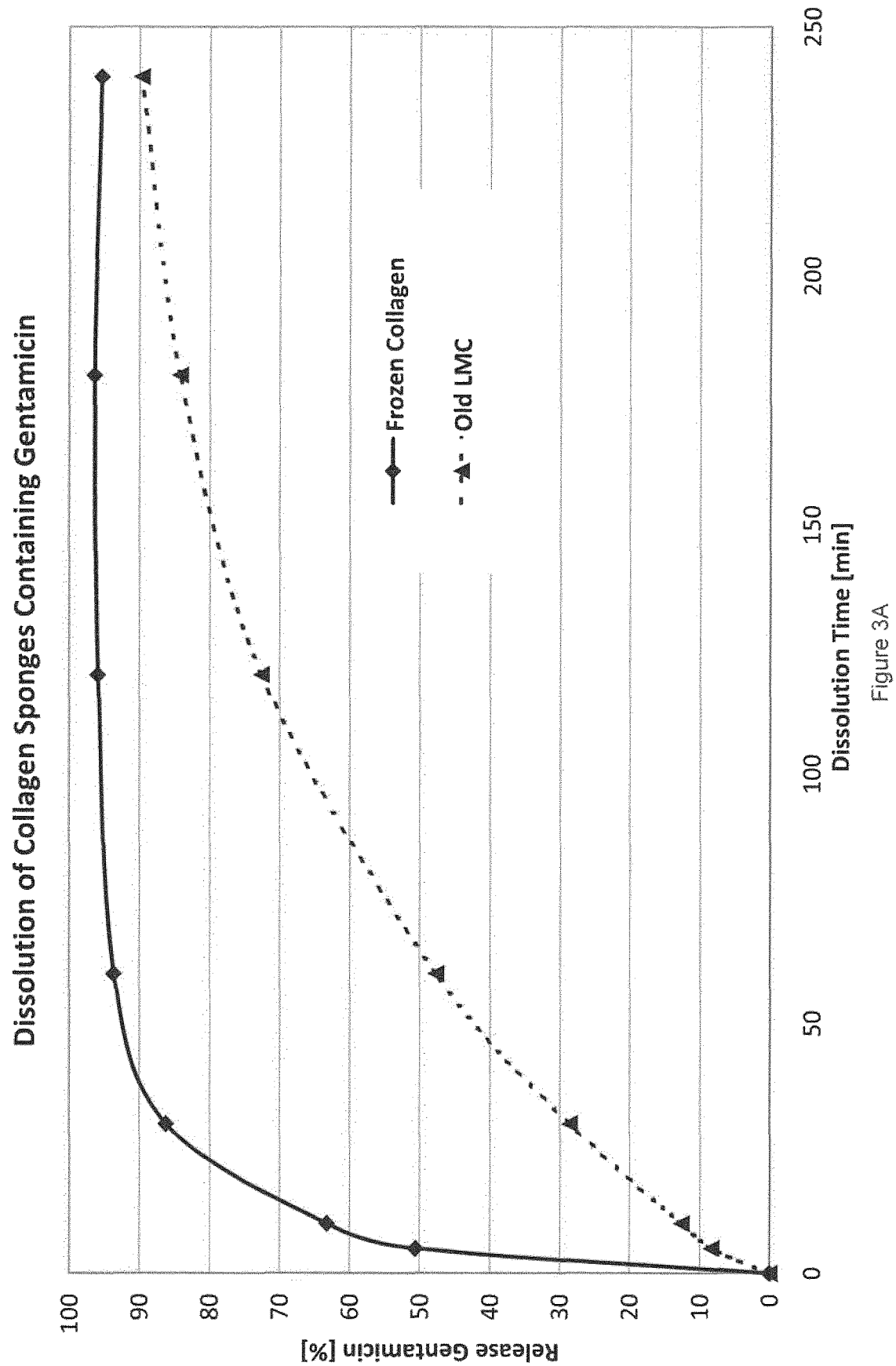
FIG. 3A is a graph illustrating the dissolution characteristic of gentamicin-containing compositions prepared from frozen collagen and dehydrated frozen collagen, which was allowed to age under ambient conditions for 3 years (old lyophilised milled collagen)
Figure 3B:
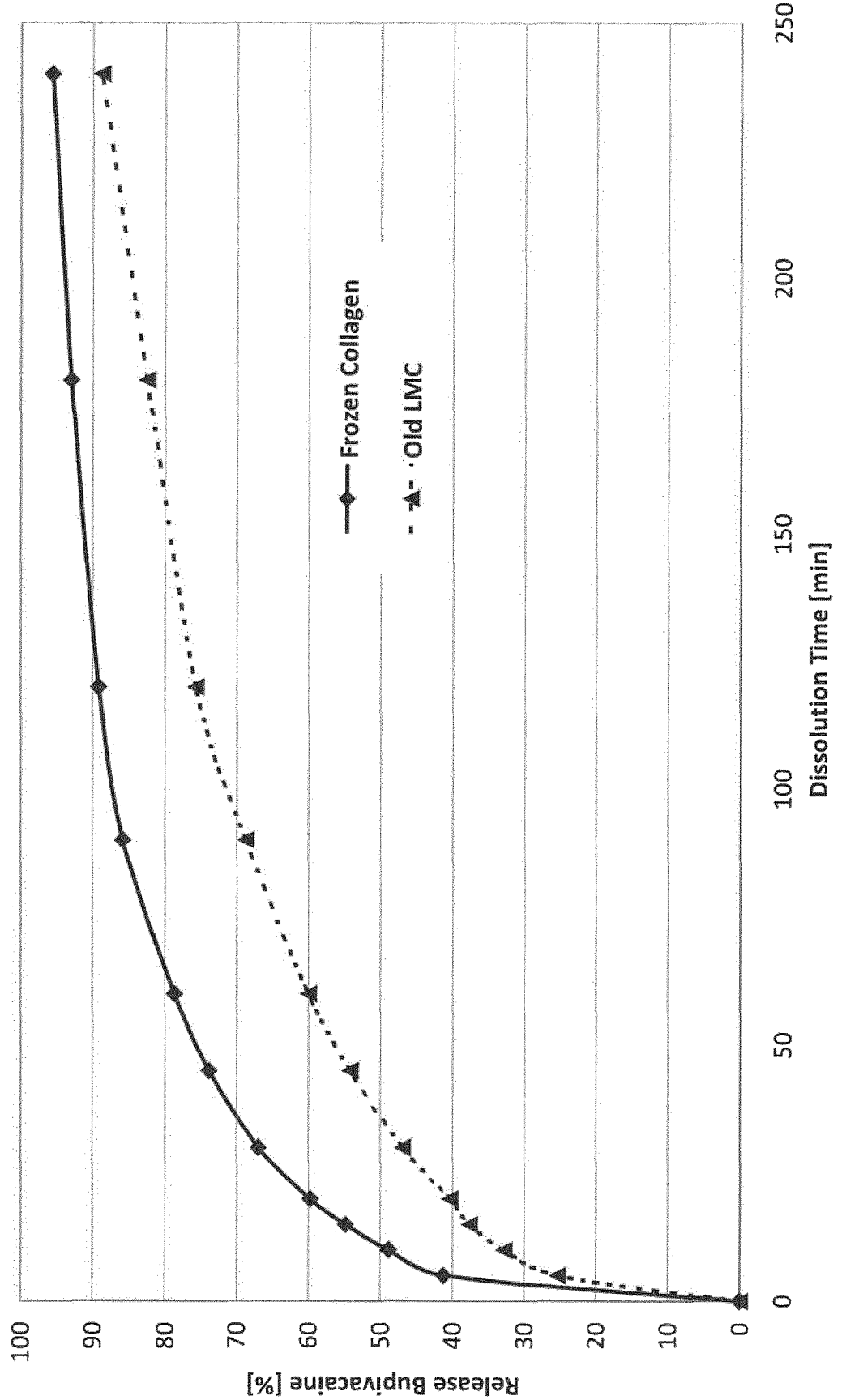
FIG. 3B is a graph illustrating the dissolution characteristic of bupivacaine-containing compositions prepared from frozen collagen and dehydrated frozen collagen, which was allowed to age under ambient conditions for 3 years (old lyophilised milled collagen)

The results of these dissolution studies demonstrate that a modified collagen according to the present invention provides a drug delivery composition, wherein the rate of release of biologically active substances from the collagen-based composition is reduced relative to those compositions made from isolated collagen without modification, thereby providing a drug delivery composition having a more sustained action of drug release (see FIGS. 3A and 3B).

Figure 8A:
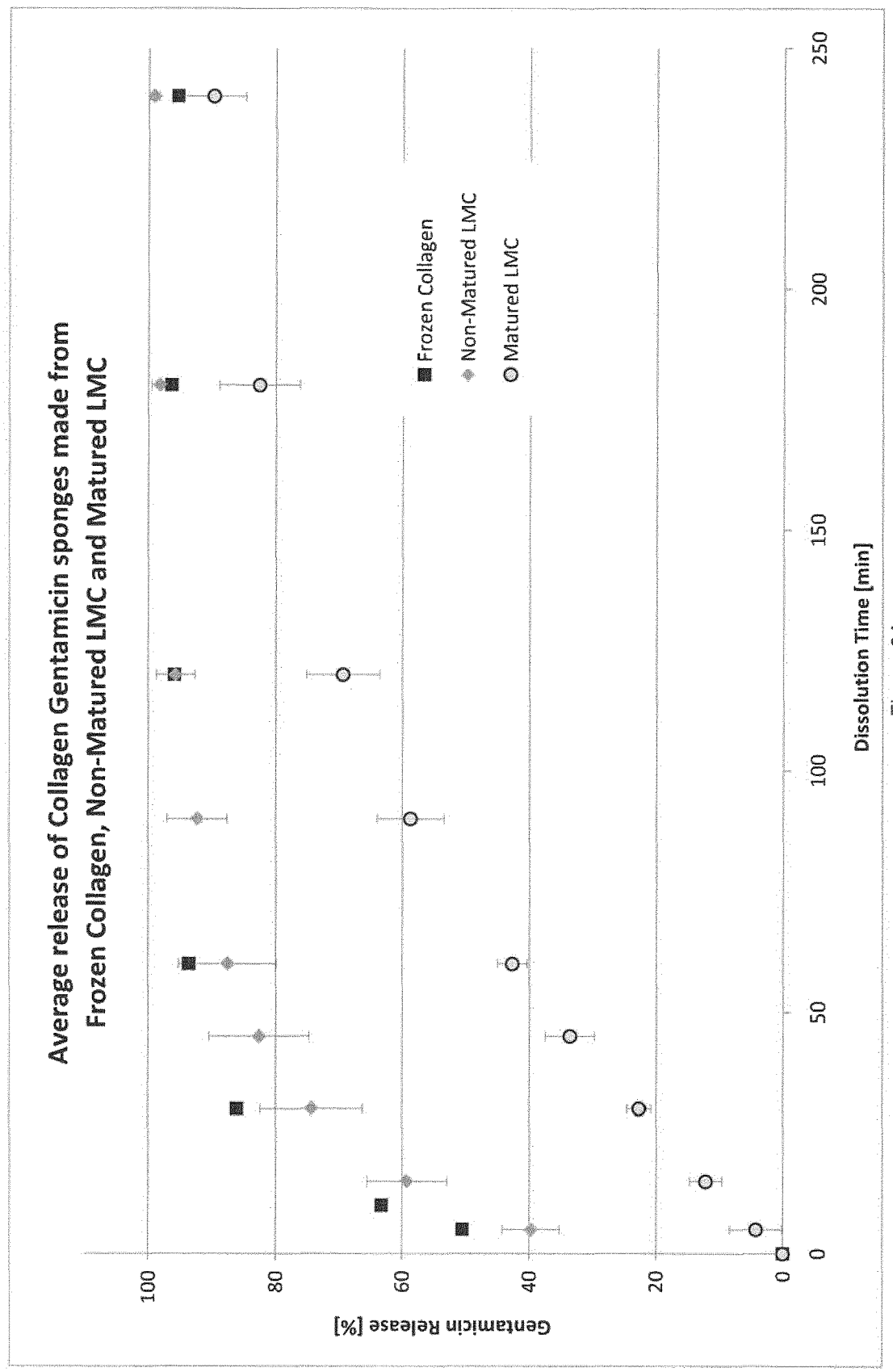
FIG. 8A is a graph illustrating the dissolution characteristic of gentamicin-containing compositions prepared from frozen collagen (FWC), dehydrated frozen collagen (non-matured LMC), and a modified collagen according to a first aspect of the present invention (LMC matured)
Figure 8B:
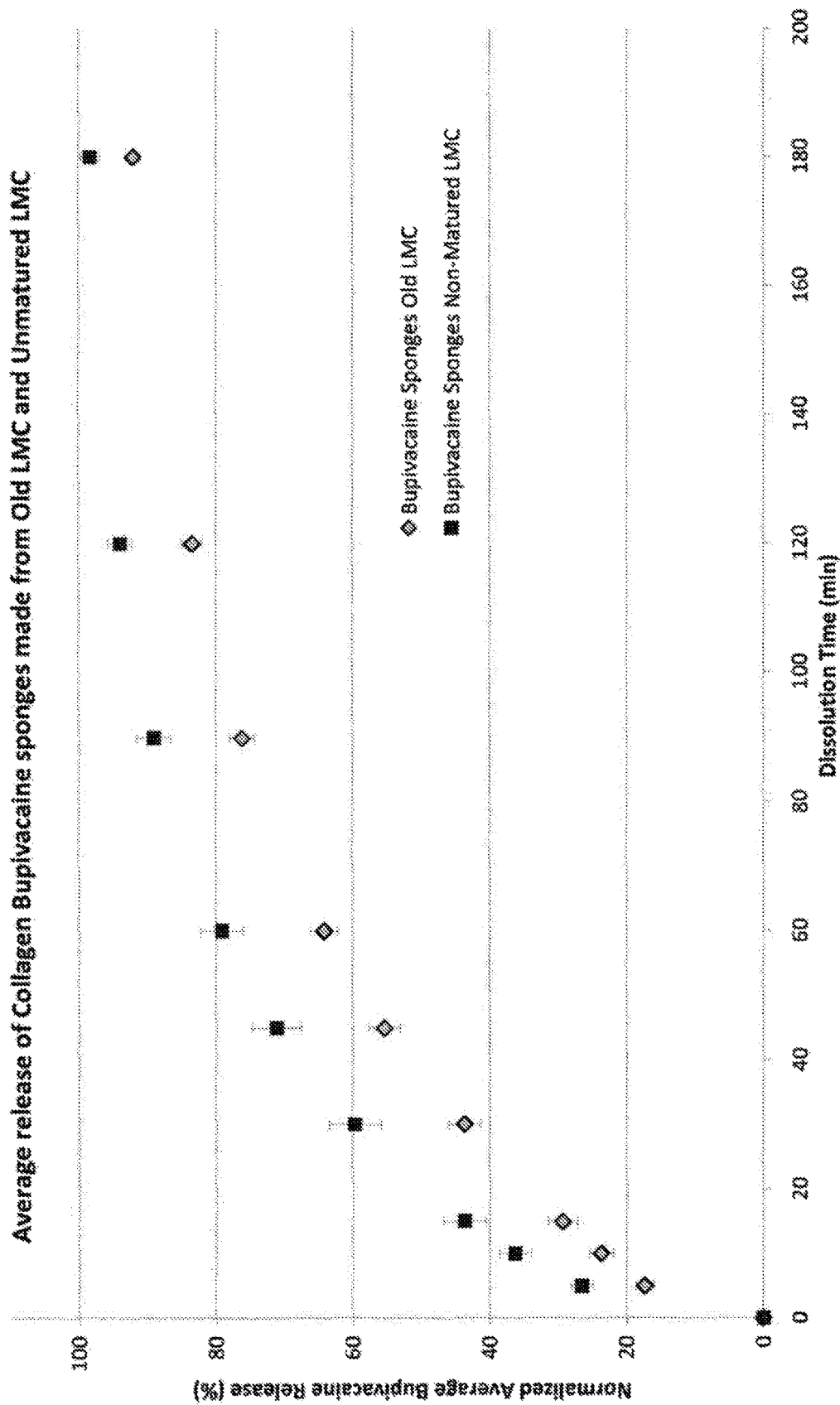
FIG. 8B is a graph illustrating the dissolution characteristic of bupivacaine-containing compositions prepared from dehydrated frozen collagen, which was allowed to age under ambient conditions for 3 years (old LMC), and dehydrated frozen collagen (non-matured LMC)

Moreover, as can be seen from FIGS. 8A and 8B, matured LMC provides a drug delivery composition, which demonstrates a significantly reduced rate of release of biologically active substances compared to compositions prepared from non-matured lyophilised LMC or frozen collagen; thereby providing a drug delivery composition having a more sustained action of drug release.

This extended release can be beneficial for collagen-based products containing active pharmaceutical ingredients (API) with good solubility in water. A retardation of release kinetics for this combination is otherwise difficult to achieve without chemical cross-linking of the drug delivery composition. Both in topical and implant administration, the extended release of the ingredient from the drug delivery composition can lead to longer therapeutic action and improved local efficacy.

Example 5—Storage

Non-matured lyophilized milled collagen (non-matured LMC) was prepared as described in Example 1; and matured by storing in polyethylene containers (bags) as described herein for up to 4 weeks. The resulting material was designated matured lyophilized milled collagen (matured LMC).

The viscosity values were measured at each of the time periods noted (1, 2, 3, and 4 weeks storage) as described in Example 3. In short, the viscosity values were measured using a Brookfield viscometer (Digital Rheometer DV-III+ with associated TC-501 Circulating Bath) at a constant shear rate ($15\ s^{-1}$) and over a temperature range from 30 to 65° C. The viscosity values of matured lyophilised milled collagen having a low moisture content of 1-2% and a high moisture content of 13-15% were measured.

Figure 9:
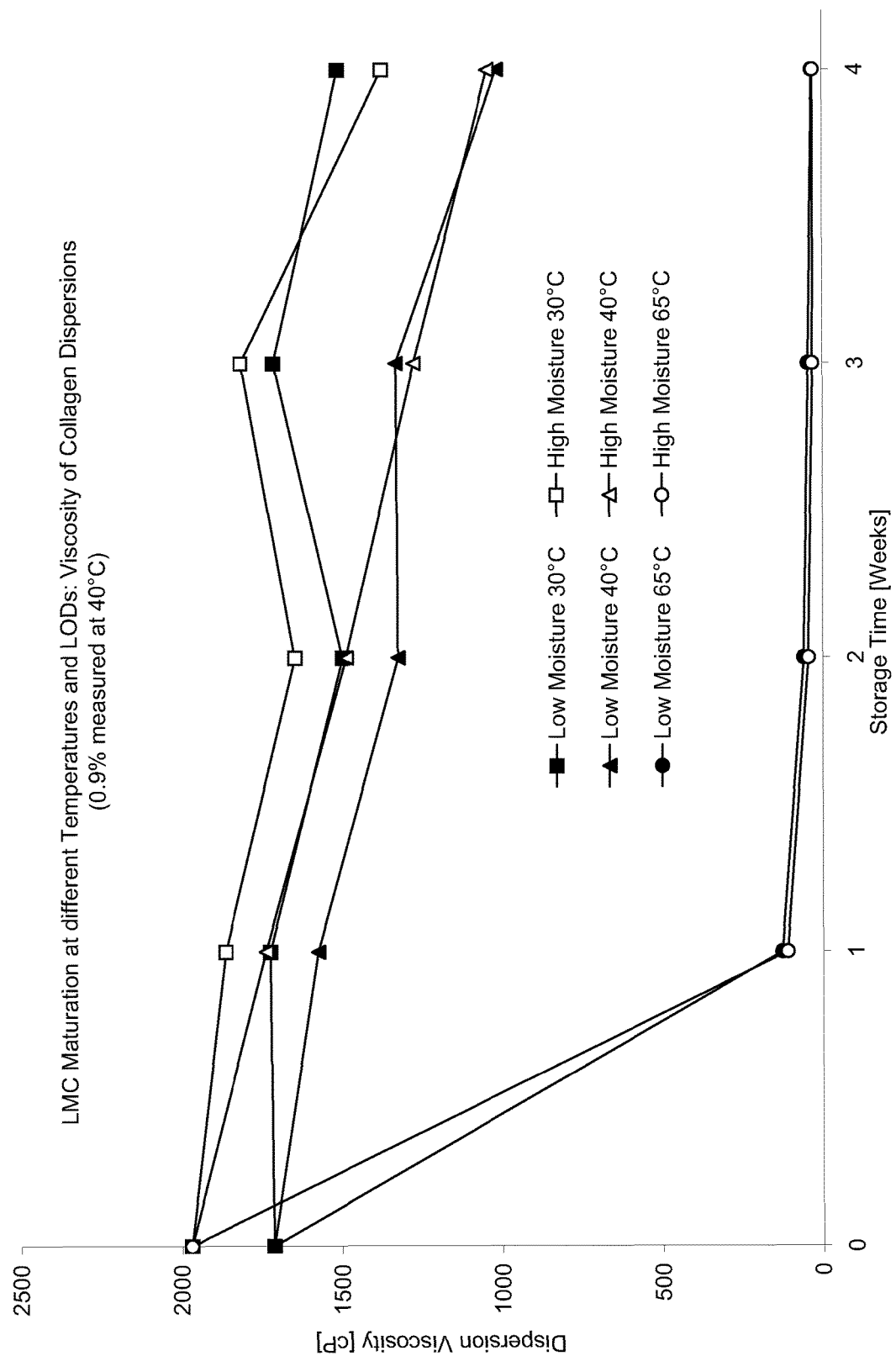
FIG. 9 is a graph illustrating the illustrating the viscosity characteristic of a modified collagen according to a first aspect of the present invention, matured for up to 4 weeks (LMC matured).

As can be seen from FIG. 9, generally, the viscosity of the matured lyophilised milled collagen is unaffected by the moisture content of the matured lyophilised milled collagen. Moreover, increasing the storage temperature accelerates the viscosity reduction of the matured lyophilised milled collagen. Certainly, maturing the lyophilised milled collagen as described herein results in improved viscosity at all investigated storage times. At lower storage temperature, the time required to reach the target viscosity is extended.

The invention claimed is:

1. A method for manufacturing a composition comprising a modified collagen, the method comprising the steps of:
    (a) providing isolated collagen;
    (b) freezing the isolated collagen to obtain frozen collagen;
    (c) dehydrating the frozen collagen to obtain dehydrated collagen;
    (d) maintaining the dehydrated collagen at a temperature of about 40° C. to about 65° C. for a period of at least one week;
    (e) preparing an aqueous dispersion of the collagen obtained in step (d);
    (f) mechanically degrading the aqueous dispersion; and
    (g) dehydrating the aqueous dispersion.

2. The method of claim 1, wherein the preparing step (e) comprises heating water to about 35° C. to about 42° C. prior to adding to the modified collagen.

3. The method of claim 1, wherein the providing step (a) comprises providing a dispersion having a concentration of about 3-30% (w/w) collagen particles.

4. The method of claim 1, wherein the freezing step comprises freezing to a temperature of about −33° C. to about −42° C.

5. The method of claim 1, wherein the dehydrating step (c) comprises removing the aqueous phase by reducing the pressure to about 0.05 to about 0.5 mbar.

6. The method of claim 1, wherein the dehydrating step (c) comprises increasing the temperature of the collagen to about +30° C.

7. The method of claim 1, wherein the dehydrating step (c) comprises at least one equilibrating step, wherein each equilibrating step comprises maintaining the temperature at a constant temperature for at least 10 minutes.

8. The method of claim 1, wherein the maintaining step is conducted at a temperature of at least 65° C. for a period of at least one week.

9. The method of claim 1, wherein the maintaining step is conducted at a relative humidity of less than 80%.

10. The method of claim 1, wherein the maintaining step is conducted for a period of at least two weeks.

11. The method of claim 1, wherein the maintaining step is conducted for a period of at least four weeks.

12. The method of claim 1, wherein the maintaining step is conducted for a period of at least six weeks.

13. The method of claim 1, wherein the maintaining step is conducted at a temperature of a bout 40° C. for a period of at least six weeks.

14. The method of claim 1, wherein the maintaining step is conducted at a tempera to re of a bout 40° C. for a period of six weeks to six months.

15. The method of claim 1, wherein the maintaining step is conducted at a temperature of a bout 40° C. for a period of six weeks to two months.

16. The method of claim 1, wherein the maintaining step is conducted at a temperature of a bout 40° C. and a relative humidity of 75% for a period of at least six weeks.

17. The method of claim 1, wherein the preparing step (e) comprises preparing an aqueous dispersion of a drug and the collagen obtained in step (d).

* * * * *